United States Patent [19]

Palladino et al.

[11] Patent Number: 5,008,380

[45] Date of Patent: Apr. 16, 1991

[54] PROCESS FOR THE CONVERSION OF DAUNORUBICIN INTO DOXORUBICIN

[75] Inventors: Gaetano Palladino; Peter MacDonald; Ettore Bigatti, all of Milan, Italy

[73] Assignee: Sicor Societa 'Italiana Corticosteroidi S.p.A., Milan, Italy

[21] Appl. No.: 269,199

[22] Filed: Nov. 9, 1988

[30] Foreign Application Priority Data

Oct. 11, 1988 [IT] Italy ............................ 22260 A/88

[51] Int. Cl.$^5$ ..................... C07H 15/24; C07H 15/00
[52] U.S. Cl. ................................. 536/6.4; 536/18.5
[58] Field of Search ........................... 536/6.4, 18.5

[56] References Cited

U.S. PATENT DOCUMENTS 3,803,124  4/1974  Arcamone et al. ................ 536/6.4

FOREIGN PATENT DOCUMENTS 0691364  5/1953  United Kingdom ............... 536/110

OTHER PUBLICATIONS

Morrison et al., *Organic Chemistry*, 3rd ed. (1979); p. 663, published by Allyn and Bacon, Inc.

*Primary Examiner*—Elli Peselev
*Attorney, Agent, or Firm*—Bucknam and Archer

[57] ABSTRACT

An improved process for the preparation of doxorubicin, by means of hydrolysis of a doxorubicin ester of a dicarboxylic acid, in acid medium.

1 Claim, No Drawings

PROCESS FOR THE CONVERSION OF DAUNORUBICIN INTO DOXORUBICIN

The present invention relates to an improved process for the preparation of doxorubicin, by means of hydrolysis of a doxorubicin ester of a dicarboxylic acid, in acid medium.

BACKGROUND OF THE INVENTION

Doxorubicin was first isolated (albeit in low yield) from the fermentation broth of Streptomyces peucetius var. caesius (U.S. Pat. No. 3,590,028).

Subsequently doxorubicin was synthesized from daunorubicin (U.S. Pat. No. 3,803,124) by halogenation with bromine or iodine in a cyclic ether containing 18-40% of methanol to give the corresponding 14-halo derivative; doxorubicin then was obtained either directly by alkaline hydrolysis of this intermediate or indirectly via 14-acetoxy daunorubicin (obtained by treatment of the 14-halo derivative with an alkali metal acetate in the presence of acetone) which was in turn subjected to alkaline hydrolysis. The overall yields (from daunorubicin hydrochloride to doxorubicin hydrochloride) claimed in the above-mentioned patent are 37% for the direct hydrolysis method (Example 1) but only 0.8% for the method using alkaline hydrolysis of the 14-acetoxy-daunorubicin intermediate (Example 2). In order to overcome the degradative side-reactions the use of various protecting groups was studied (Examples 5 and 6). This complication, however, did not lead to any improvement in the overall yield and indeed the products were isolated, in extremely low yields, only after chromatographic purification.

WO86/00073 claims an improved method for the bromination of daunorubicin hydrochloride using conditions which lead to ketal formation, principally the 13,13-dimethoxy ketal, thus stabilizing the intermediate 14-bromo-daunorubicin. The method described for the conversion of this intermediate into doxorubicin hydrochloride consists of treatment with diluted hydrobromic acid in acetone leading to the free ketone, which is treated without isolation with sodrum formate to give the 14-formyloxy derivative. Hydrolysis of this 14-formyloxy intermediate could be achieved under milder alkaline conditions (pH 7.6 to 8.0) than those used for the hydrolysis of the 14-acetoxy intermediate (pH 10.3). Application of this modified method, however, only gives a very slight improvement in the overall yield from daunorubicin hydrochloride to doxorubicin hydrochloride (increase from 37% to 42.4%).

SUMMARY OF THE INVENTION

It has now surprisingly been found that certain novel esters of doxorubicin may be hydrolyzed under acidic conditions, and that the yield of doxorubicin thus obtained is much higher than that obtained by alkaline hydrolysis of previously described esters, e.g. doxorubicin acetate, or by direct alkaline hydrolysis of 14-bromo-daunorubicin. These acid-hydrolyzable esters are valuable intermediates in an improved process for the production of doxorubicin from daunorubicin.

In a preferred embodiment of the invention these acid-hydrolyzable esters are prepared from 14-bromo-daunorubicin (either in the free or ketalized form) and hydrolyzed without isolation to give doxorubicin in high yield.

In a specially preferred embodiment a 14-bromo-daunorubicin ketal, preferably the diethyl ketal, is treated in water with an acid, e.g. hydrochloric, hydrobromic or, preferably, oxalic acid in order to form free 14-bromo daunorubicin, which without isolation is immediately treated at a pH below 6 with an alkali metal salt of an acid, preferably oxalic acid, which forms an acid-hydrolyzable ester with doxorubicin, and the resulting doxorubicin ester is hydrolyzed in situ to yield doxorubicin.

Also claimed are acid-hydrolyzable esters of doxorubicin at physiological pH.

A particularly preferred ester is doxorubicin 14-oxalate.

A further aspect of the invention is a process wherein 14-bromo-daunorubicin (in either the free or ketalized form) is treated at pH 1-6 with aqueous oxalic acid solution in the absence of other solvents to give doxorubicin 14-oxalate.

In yet another aspect of the invention 14-bromo-daunorubicin (in either the free or ketalized form) is treated with aqueous oxalic acid solution in the absence of other solvents to give doxorubicin.

In a preferred embodiment of the invention the bromination of daunorubicin is carried out under conditions which form the diethoxy ketal (14-bromo-daunorubicin 13,13-diethoxy ketal).

In another preferred embodiment of the invention an aqueous solution of the salt of doxorubicin with oxalic acid is adsorbed onto a macromolecular resin and thereafter the pure product is obtained by selective desorption using a mixture of water, methanol, and hydrochloric acid followed by crystallization from ethanol/acetone/hydrochloric acid.

Alternatively, doxorubicin may be conveniently isolated from the aqueous hydrolysis mixture as the salt with oxalic acid. This salt has a low solubility in water thus permitting isolation by direct crystallization from ther reaction mixture. If required the salt with oxalic acid is then converted into doxorubicin hydrochloride by treatment with ethanol/hydrochloric acid followed by precipitation with acetone.

Also claimed as a new chemical entity is doxorubicin oxalate.

DETAILED DESCRIPTION OF THE INVENTION

Surprisingly it has been found that certain esters of doxorubicin do not require alkaline conditions for hydrolysis.

The process of the invention takes advantage of that in order to achieve the transformation of the readily available intermediate 14-bromo-daunorubicin (either in the free or ketalized form) into doxorubicin in a one-pot high-yielding process.

A particular advantage of the process is that the intermediate 14-bromo-daunorubicin (either as the free or ketalized form), obtained from daunorubicin by bromination in a manner known per se, is transformed directly into doxorubicin without any use of organic solvents. The use of water as the reaction medium represents a considerable saving in solvent costs as well as having ecological and safety advantages.

The preferred conditions of the novel process consist in treatment of 14-bromo-daunorubicin (in either the free or ketalized form), as an aqueous solution or suspension, with oxalic acid, initially at pH 1-2 in order to hydrolyze a ketal group, if present, and subsequently raising the pH to 2-6, preferably 3-5, in order to convert the free 14-bromo-daunorubicin into doxorubicin.

It has been found that in contrast to the previously described 14-bromo-daunorubicin 13,13-dimethoxy ketal, the corresponding 13,13-diethoxy ketal offers significant advantages in that this latter compound has a remarkably low solubility in water and this enables the intermediate to be isolated and pufified in a simple manner on an industrial scale; furthermore the diethoxy derivative is much more easily and efficiently deketalized. Thus whereas deketalization of the dimethoxy ketal requires the use of a mineral acid (hydrobromic) as well as use of a solvent capable of trans-ketalization (acetone), the corresponding diethoxy ketal may be hydrolyzed in water using the same organic acid employed in the subsequent steps of substitution and hydrolysis. The preferred organic acid is oxalic acid.

A further advantage conferred by the use of the dibasic oxalic acid is that the hydrolysis reaction mixture contains doxorubicin as its salt with oxalic acid and this salt is very readily adsorbed onto a macromolecular adsorption resin, in contrast to salts with monobasic acids such as acetic, formic or hydrochloric, possibly because of the much higher molecular weight of this salt (formed from two molecules of doxorubicin with one molecule of oxalic acid) with respect to salts with monobasic acids. Once adsorbed onto the macromolecular adsorption resin, doxorubicin may be washed free of inorganic salts and other impurities, using for example water, and then selectively desorbed using a suitable mixture of water, methanol and hydrochloric acid. Purified doxorubicin hydrochloride may then be obtained by concentration and crystallization from ethanol-/acetone/hydrochloric acid.

The following non-limiting examples illustrate in more detail the invention.

EXAMPLES

Example 1

10 g 14-bromo-daunorubicin, obtained as described in U.S. Pat. No. 3,803,124, was dissolved in 1 liter water containing 25 g oxalic acid and pH was adjusted to 3.5-4.0 with sodium bicarbonate. The solution was stirred at 45°-50° C. for 48 hours. On cooling doxorubicin precipitated as the salt with oxalic acid (7 g, assay 90%).

Example 2

To a solution of 10 g of daunorubicin hydrochloride in 200 ml of absolute ethanol and 200 ml dioxane containing 20 ml triethylorthoformate was added at a temperature maintained at 16°-18° C. 2 g hydrogen bromide gas followed by 3.5 g bromine. After completion of the bromination, which was accompanied by ketalization, the excess of bromine was removed by addition of 0.5 g of sodium metabisulfite and after adjusting pH to about 4 using sodium bicarbonate, the reaction mixture was evaporated using a rotary evaporator to a semi-crystalline residue. The residue of 14-bromo-daunorubicin 13,13-diethoxy ketal was taken up in 600 ml of water and treated with 40 g oxalic acid and the solution was stirred at room temperature 20°-25° C. overnight in order to remove the ketal group. The solution was adjusted to pH 3.7 using 10% sodium carbonate solution and held at 50 for 48 hours, after which time conversion into doxorubicin was complete (formation of the intermediate doxorubicin 14-oxalate and subsequent hydrolysis of the oxalate group). The product was isolated by absorption of the hot solution onto a column of XAD 761 phenolic resin and subsequent elution with a mixture of methanol and dilute hydrochloric acid. Evaporation of the eluates under reduced pressure afforded doxorubicin hydrochloride which after recrystallization from ethanol/dilute hydrochloric acid/acetone yielded pure doxorubicin hydrochloride identical with an authentic sample. Yield of purified product: 6.0 g.

Example 3

3 g of 14-bromo daunorubicin 13,13-diethoxy ketal, prepared as described in Example 2 from 2.5 g of daunorubicin hydrochloride and isolated by filtration after trituration with a small volume of water, was stirred overnight at 25°-30° C. in 150 ml of a 5% aqueous solution of oxalic acid, at which time hydrolysis of the ketal group was complete. The pH was adjusted to 3.5 using a 5% solution of sodium bicarbonate and then the reaction mixture was kept at 50° C. for 2 days, after which time quantitative HPLC analysis (using the conditions of USP XXI) of the reaction mixture showed the presence of 1.75 g of doxorubicin (as the free substance). Isolation by preparative HPLC using a RP-18 reverse-phase silica gel column gave 1.5 g of doxorubicin hydrochloride having a purity of 98.9%.

We claim:

1. A process for the preparation of doxorubicin, which consists of reacting 14-bromo-daunorubicin 13,13-diethylketal in aqueous medium, in the absence of organic solvents, with oxalic acid first at pH 1-2 and, after hydrolysis of the ketal group, at pH 2-6 to obtain doxorubicin 14-oxalate ester, hydrolyzing said ester and isolating doxorubicin from the reaction mixture.

* * * * *